US005484610A

United States Patent [19]
Bae

[11] Patent Number: 5,484,610
[45] Date of Patent: Jan. 16, 1996

[54] PH AND TEMPERATURE SENSITIVE TERPOLYMERS FOR ORAL DRUG DELIVERY

[75] Inventor: You H. Bae, Salt Lake City, Utah

[73] Assignee: MacroMed, Inc., Salt Lake City, Utah

[21] Appl. No.: 636,747

[22] Filed: Jan. 2, 1991

[51] Int. Cl.$^6$ ............................ A61K 9/14; A61K 9/32; A61K 9/58; A61K 47/32; C08F 220/06; C08F 220/52

[52] U.S. Cl. ...................... 424/487; 424/482; 424/463; 424/487; 526/263; 526/265; 526/303.1; 526/307.6; 526/291; 526/292.95; 526/916; 514/772.6; 514/772.5

[58] Field of Search .................................... 424/463, 482, 424/487, 78; 526/263, 307.6, 292.95, 916; 514/772.6, 772.5

[56] References Cited

U.S. PATENT DOCUMENTS

| | | | |
|---|---|---|---|
| 3,927,199 | 12/1975 | Micchelli et al. | 424/47 |
| 4,395,524 | 7/1983 | Emmons et al. | 526/307.2 |
| 4,795,436 | 1/1989 | Robinson | 424/462 |
| 4,842,852 | 6/1989 | Nowak, Jr. et al. | 526/307.6 |
| 5,037,863 | 8/1991 | Kozakiewicz et al. | 526/306 |
| 5,047,244 | 9/1991 | Sanvordeker et al. | 424/486 |
| 5,053,228 | 10/1991 | Mori et al. | 424/78.31 |
| 5,057,560 | 10/1991 | Mueller | 524/22 |

*Primary Examiner*—Edward J. Webman
*Attorney, Agent, or Firm*—Thorpe North & Western

[57] ABSTRACT

Terpolymers which are sensitive to pH and temperature are useful carriers for conducting bioactive agents through the gastric juices of the stomach in protected form. Such terpolymers swell at the higher physiologic pH of the intestinal tract causing release of the bioactive agents into the intestine. The terpolymers are linear and are made up of 35 to 99 wt % of a temperature sensitive component, which imparts to the terpolymer LCST (lower critical solution temperature) properties below body temperatures, 1 to 30 wt % of a pH sensitive component having a $pK_a$ in the range of from 2 to 8 which functions through ionization or deionization of carboxylic acid groups to prevent the bioactive agent from being lost at low pH but allows bioactive agent release at physiological pH of about 7.4 and a hydrophobic component which stabilizes the LCST below body temperatures and compensates for bioactive agent effects on the terpolymers. Such terpolymers provide for safe bioactive agent loading, a simple procedure for dosage form fabrication and the terpolymer functions as a protective carrier in the acidic environment of the stomach and also protects the bioactive agents from digestive enzymes until the bioactive agent is released in the intestinal tract.

17 Claims, 3 Drawing Sheets

PH AND TEMPERATURE SENSITIVE TERPOLYMERS FOR ORAL DRUG DELIVERY

BACKGROUND OF THE INVENTION

This invention relates to pH and temperature sensitive terpolymers which are useful as carriers or coating materials for oral drug delivery. More particularly, this invention relates to terpolymers having pH sensitive, temperature sensitive and hydrophobic components. This class of terpolymers allows for drug-laden compositions to be orally ingested, pass through the acidic environment of the stomach and into the intestinal tract where the drugs are released in response to temperature and pH conditions.

Most polymeric controlled drug delivery systems have been developed to achieve desirable release rates. A zero-order (or constant-rate) of drug delivery is preferable to achieve optimal therapeutic effects. Zero-order release of a drug from monolithic polymer devices cannot generally be obtained because the drug concentration gradient within the polymer matrix falls with time. Various types of approaches have been developed to improve release rates. One approach includes introduction of a diffusional barrier on the surface of a polymer matrix. Lee et al, "Drug Release from Hydrogel Devices with Rate-Controlling Barriers", *J. Membr. Sci.*, 7, 293–303 (1980), disclose methods for introducing rate-controlling barriers on the surface of monolithic hydrogel devices prepared from poly-HEMA (polyhydroxyethyl methacrylate) and a copolymer of HEMA and MEEMA (methoxyethoxyethyl methacrylate). The rate limiting barrier was produced in monolithic devices by soaking in an ethanolic solution of the crosslinking agent EGDMA (ethylene glycol dimethacrylate) followed by UV (ultraviolet) radiation. Release of progesterone from such devices in vitro was zero-order. A different method of improving release is to control hydrogel swelling. Hopfenberg et al., "Swelling-Controlled, Constant Rate Delivery Systems", *Polym. Eng. Sci.* 18 1186–1191 (1978) address materials and conditions required for in vitro constant rate absorption of a liquid into a glassy polymer to produce prototype devices for constant rate delivery of a solute (drug), molecularly dispersed within the polymer, to the surrounding liquid environment and discuss the development of such devices for the swelling-controlled release of drugs. In a similar vein, crystalline/glassy transition controlled release is discussed by Graham et al., "Hydrogels for Controlled Drug Delivery", *Biomaterials* 5, 27–36 (1984). Lee, "Novel Approach to Zero-order Drug Delivery Via Immobilized Nonuniform Drug Distribution in Glassy Hydrogels", *J. Pharm. Sci.* 73, 1344–1347 (1984) refers to improving release by means of a loading method utilizing a controlled-extraction process on initially dry, drug-loaded hydrogels to generate an inflection-point-containing drug concentration profile followed by a vacuum freeze-drying step to rapidly remove the swelling solvent and immobilize in situ a nonuniform drug distribution. An approach wherein the principal energy source governing the release of drugs from polymeric matrices is osmotic in nature is discussed by Gale et al, "Use of Osmotically Active Therapeutic Agents in Monolithic Systems", *J. Memb. Sci.* 2, 319–331 (1980). Mueller et al., "Gradient-IPN-Modified Hydrogel Beads: Their Synthesis by Diffusion-Polycondensation and Function as Controlled Drug Delivery Agents", *J. App. Polym. Sci.* 27, 4043–4064 (1982), discuss the utilization of osmotic and gradient effects in using IPN (interpenetrating polymer network) membranes and matrices to improve drug delivery rates. The use of heterogeneous interpenetrating polymer network matrices for the controlled release of drugs is further disclosed by Bae et al., U.S. Pat. No. 4,921,287 which issued Jun. 5, 1990. The network disclosed is a heterogeneous matrix formed from a hydrophilic component such as polyethylene oxide (PEO) or poly(N,N'-dimethyl acrylamide-co-styrene) ($DMM_m$-co-styrene) and a hydrophobic component such as styrene, an alkyl methacrylate or polytetramethylene ether glycol. The relative amounts of the two components, or "domains", can be varied, as can the diffusivities and solubilities of the drug combinations to be loaded therein, to control and change, as desired, the time release profile of incorporated drug. The control of release from matrices by varying the geometry is disclosed by Hsieh, et al. "Zero-Order Controlled-Release Polymer Matrices for Micro- and Macromolecules", *J. Pharm. Sci.* 72, 17–22 (1983). These are but representative of numerous methods/and or devices which have been proposed as a means for improving delivery of orally ingested drug-laden compositions. However, approaches heretofore made generally suffer from complicated fabrication procedures which may not be economical, practical, and may not even be suitable for preparing polymers for oral drug delivery. One problem is that the release of the incorporated drug is at a predetermined rate regardless of environmental conditions. Perhaps even more detrimental is that the drug-laden polymer must pass through the high acidic environment of the stomach where the drug may be released and/or undergo rapid hydrolysis or, in the case of peptides and proteins, denaturation and hydrolysis.

Preferably, drugs in dosage forms for human applications should be incorporated into the carrier system using straightforward procedures under clean, nontoxic conditions to maintain the activity of the labile drugs. Drug incorporation is generally performed by the polymerization of monomeric materials in the presence of drugs, the solvent casting of drug polymer solutions or by a solvent sorption technique of polymerized and purified polymers. In the pre-polymer drug incorporation methods the purification of the final product is often neglected or impossible to accomplish. This leaves unreacted or other undesirable components in the product which may lead to difficulties in clinical applications. In cases of solvent casting or solvent sorption techniques, nontoxic solvents are used for drug/polymer dissolution or as the swelling agent. These methods are considered beneficial for some active agents in stable organic solvents. However, polypeptide or protein drugs undergo conformational changes or denaturation, even with relatively nontoxic alcoholic solutions.

Polymers showing lower critical solution temperature (LCST) in water are desirable for loading of bioactive polypeptides and proteins. This means that an aqueous polymer solution undergoes a phase separation (precipitation) when heated above it's LCST. This results in temperature sensitive polymers which are soluble in water at low temperatures but which are solidified at body temperature can act as carriers for protein and polypeptide type compounds. To minimize problems of hydrolysis or degradation in the stomach, it would also be desirable to block gastric drug release through the use of pH sensitive materials which are rigid or insoluble at stomach pH, thereby preventing drug release, but which will dissolve or swell in the normal physiological pH of the intestinal tract allowing drug release therein.

The formation of insoluble crosslinked hydrogel copolymers having both pH and temperature sensitive properties as carriers for bioactive agents of the protein or polypeptide category have recently been reported. Dong et al., "pH Sensitive Hydrogels Based on Thermally Reversible Gels for Enteric Drug Delivery", *Proc. Intern. Symp. Control. Rel. Bioact. Mater.*, 16 95–96 (1989) and Park et al., "Synthesis, Characterization, and Application of pH/Temperature Sensitive Hydrogels", Proc. Intern. Symp. Control. Rel. Bioact. Mater., 17 112–113 (1990) refer to such hydrogel systems. Dong et al., show the incorporation of acrylic acid (AAc) into LCST heterogels formed from the combination of a 1/1 ratio of Poly(N-isopropylacrylamide), (NIPAAm) and vinyl terminated polydimethylsiloxane (VTPDMS). These hydrogels are stated to be sensitive to both pH and temperature when used as an insoluble matrix system for the enteric delivery of indomethacin, a non-steroid anti-inflammatory drug. Dong et al. prepared hydrogels having from 2 to 10 moles of AAc per 100 moles of NIPAAm. They found only moderate swelling of the gels at a pH of 1.4 but extensive swelling at pH of 7.4. Swelling increased with AAc content. Only negligible amounts of indomethacin were released at the gastric fluid pH of 1.4 but release increased at the higher pH. These copolymers were above their LCST at the physiological temperature of 37° C. The release rate at pH 7.4 was relatively constant suggesting a swelling-controlled mechanism.

Park et al. state that for such hydrogels to function properly, the gel should exhibit a sharp volume change with small pH changes near physiological pH (7.4) and at body temperature (37° C.). Park et al. prepared a series of pH sensitive, cationic copolymeric hydrogels, based on a thermally reversible hydrogel exhibiting a phase transition behavior, which were characterized in terms of pH-dependent swelling properties. The gels were prepared by the copolymerization of NIPAAm and N',N'-dimethylaminopropylmethacrylamide (DMAPMAAm) in various molar ratios in the presence of a small amount of a crosslinker. To test a self-regulated insulin release from this hydrogel matrix, insulin crystals and glucose oxidase were co-entrapped within a hydrogel matrix (97/3 molar ratio of NIPAAm/DMAPMAAm) which exhibited a pH-dependent phase transition at about pH 7.4 at 37° C. as well as a temperature-dependent phase transition under the same conditions. Insulin release profiles from the hydrogel matrix were studied by modulating the external pH, glucose concentration, temperature and thermal cycling operation. The water content of the gel was found to be dependent on both pH and temperature with the gel swelling in the low pH region due to the ionic repulsion of the protonated amine groups and collapsing at high pH values because of unprotonated amine groups and the thermally-induced collapse of the neutral gel. It was found that insulin delivery from the gel was controlled by modulating temperature. However, there were neither pH nor glucose responsive insulin releases.

The copolymers reported by both Dong et al. and Park et al. are pH/temperature sensitive hydrogels formed using vinyl terminated polydimethylsiloxane (VTPDMS) which results in crosslinked and insoluble gels under any conditions. In other words, once formed by polymerization, the solubility of these gels cannot be changed. Therefore, these gels are sensitive to pH and temperature only by swelling characteristics and not by solubility parameters. Drugs or bioactive agents can be incorporated into these gels only by solvent sorption methods or by loading concurrently during the polymerization process. Thus, these polymers suffer the same disadvantages of drug incorporation and purification referred to above.

It has been found that the LCST of polymers is affected by comonomers in such a way that hydrophilic comonomers cause the LCST to occur at higher temperatures whereas hydrophobic comonomers lower the LCST. The result is that hydrophilic pH sensitive components affect the temperature sensitive polymer properties by shifting the LCST of a temperature sensitive polymer to higher temperatures. When the LCST is above the physiological body temperature (37° C.), drug release from a hydrogel will not be controllable because of the increased solubility or swellability of the polymer. Also, there would be difficulties in the preparation of dosage forms of such formulations.

It would be desirable to provide pH and temperature sensitive polymers which are truly soluble at temperatures below their LCST, which counteract the effects of pH sensitive components on the LCST of the polymer, which can be prepared in relatively pure form and wherein the drug loading and final dosage form can be determined by a variety of techniques such as drop precipitation and coating.

OBJECTS AND BRIEF SUMMARY OF THE INVENTION

It is therefore an object of the present invention to provide soluble pH and temperature sensitive terpolymers having a LCST below physiological body temperature.

It is also an object of the invention to provide soluble terpolymers that have the above stated properties which are capable of serving as carriers of drugs or bioactive agents and bioactive proteins and polypeptides in particular.

A still further object of this invention is to provide terpolymers suitable for oral drug ingestion and intestinal tract delivery which are soluble at low temperatures and relatively neutral pH onto which bioactive agents can be mixed, which precipitate when in acidic aqueous media at physiological temperature and which swell at relative neutral pH and physiological temperatures releasing the bioactive agent contained thereon at a controlled release rate.

These and other objects may be obtained by means of linear terpolymers composed of three components, i.e. temperature sensitive, pH sensitive and hydrophobic components. These combinations incorporate into the terpolymers the desired pH and temperature sensitive features while having solubility characteristics providing a LCST well below body temperatures in the 35°–40° C. range. Such hydrogels provide for safe drug loading, a simple procedure for dosage form fabrication and allow the drug-laden polymer to function as a protective carrier in the acidic environment of the stomach and also from digestive enzymes until the bioactive agent is released in the intestinal tract.

DETAILED DESCRIPTION OF THE INVENTION AND PREFERRED EMBODIMENTS

The invention is directed to soluble linear terpolymers made up of three components which function in a manner to be hereinafter described to impart pH and temperature sensitive properties to the polymer while, at the same time, providing for polymers which are soluble at low temperatures but which have a LCST, particularly at low pH, which is considerably lower than physiological temperatures.

The temperature sensitive portion of the terpolymers are derived from monomers which impart the LCST properties to the terpolymer product. In other words, they have properties which enable the terpolymer to be water soluble at cold temperatures, i.e. about 1°–5° C., but undergo a phase separation (precipitation) when heated up to ambient temperatures, i.e. about 6°–40° C. If used alone as a homopolymer, it would not allow for drug release at body temperatures because of insufficient water swelling at about 37° C.

Temperature sensitive components are made up of monomers or mixtures of such monomers polymerizable by free radical or ionic initiation which results in terpolymers having a LCST in aqueous systems which is below that of body temperature. Suitable are the N-alkyl or N,N-dialkyl substituted acrylamides or methacrylamides of the formula:

where R is hydrogen or methyl, $R^1$ is a member selected from the group consisting of lower alkyl and lower alkoxyalkyl and $R^2$ is a member selected from the group consisting of hydrogen, lower alkyl and lower alkoxyalkyl with the proviso that $R^1$ and $R^2$ can combine as an akylene —$(CH_2)_n$— chain to form a N-cyclic structure where n is an integer of 4 to 6. n is preferably 5. By lower alkyl or alkoxy is meant a straight or branched carbon chain containing from one to eight carbon atoms and preferably from one to five carbon atoms. Mixtures of one or more of the above monomers may also be utilized as temperature sensitive components.

Exemplary of such temperature sensitive monomers are those selected from the group consisting of N-isopropylacrylamide, N,N-diethylacrylamide, acryloylpiperidine, N-ethylmethacrylamide, N-n-propylacrylamide and N-(3'-methoxypropyl)acrylamide. The preferred temperature sensitive monomers are the lower alkyl acrylamides which are selected from the group consisting of N-isopropylacrylamide, N,N'-diethylacrylamide and N-n-propylacrylamide.

These temperature sensitive monomers make up from about 35 to 99% by weight, and preferably from about 80 to 98% by weight, of the terpolymer.

The pH sensitive components are those containing acid groups having a $pK_a$ in the range of from 2 to 8. The pH sensitive components function through ionization or deionization of carboxylic acid groups to prevent the drug from being lost at a low pH but allows drug release at a physiological pH of about 7.4. Such pH sensitive components are relatively hydrophobic at low pH but hydrophilic at high pH. They are comprised of unsaturated monomers containing one or more carboxylic acid groupings. The pH sensitive components have the formula:

wherein R' is a member selected from the group consisting of hydrogen, lower alkyl, lower alkenyl, aryl, substituted aryl, lower alkoxy, aryloxy, hydroxy, carboxyloweralkyl, amino, substituted amino, amido and substituted amido; A is a member selected from the group consisting of lower alkylene, lower alkenylene, phenylene and substituted derivatives thereof, p is a numeral ranging from 0 to 3, $Y^1$ is a member selected from the group consisting of hydrogen, lower alkyl, lower alkenyl, aryl, carboxyloweralkyl, hydroxyloweralkyl, hydroxy and chloro. $Y^2$ is a member selected from the group consisting of hydrogen, lower alkyl, lower alkenyl, carboxy, carboxyloweralkyl, carboxyloweralkenyl, carboxyalkenylaryl, hydroxy, hydroxyalkyl, aroyl, carbamoyl, N- and N,N- loweralkyl, loweralkenyl or aryl substituted carbamoyl, loweralkyl carbamoyl, 5-norborneyl and chloro. By aryl is preferably meant single ring aromatic groups such as phenyl, pyridyl, pyrryl, furyl, thienyl and the like and substituted derivatives thereof with phenyl being most preferred. Whenever the term "substituted" or "substituent" is used in this application such terminology is inclusive of functional groups commonly substituted on the group referred to which do not interfere with the intended functioning of that grouping for the purpose it is being used. In its preferred embodiment p is 0 and the unsaturation, relative to the carboxylic acid, is preferably between the α,β carbon atoms. Mixtures of one or more of the above monomers may also be utilized as pH sensitive components.

Exemplary of such pH sensitive monomers are those selected from the group consisting of 2-acetamidoacrylic acid, acrylic acid, cis-aconitic acid, trans-aconitic acid, allylacetic acid, 2-allylphenoxyacetic acid, β-benzoacrylic acid, 2-chloroacrylic acid, crotonic acid, N,N-di-n-butylmaleamic acid, fumaric acid, N,N-diethylmaleamic acid, dihydroxymaleic acid, itaconic acid, 3,3-dimethylacrylic acid, N-ethylmaleamic acid, trans-2-hexenoic acid, trans-3-hexenoic acid, methacrylic acid, maleic acid, 5-norbornene-2-acrylic acid, trans-2-pentenoic acid, 1,4-phenylenediacrylic acid, N-phenylmaleamic acid, vinylacetic acid, 2,4-hexadienonic acid, 4-vinylbenzoic acid and 2-vinylpropionic acid.

Preferred pH sensitive components are acrylic acid or methacrylic acid derivatives having the following formula:

where R" is a member selected from the group consisting of H and methyl and $Y^1$ and $Y^2$ have the meanings given above but $Y^1$ is preferably a member selected from the group consisting of hydrogen, lower alkyl, lower alkenyl, hydroxy, and lower carboxyalkyl and $Y^2$ is preferably a member selected from the group consisting of hydrogen, lower alkyl, lower alkenyl, carboxy, carbamoyl and substituted carbamoyl. Acrylic and methacrylic acids are most particularly preferred.

This component enhances the solubility of the resulting terpolymers at pH 7.4 and low temperatures of about 4° C. This is considered optimal for peptide drug loading and also allows for drug release at pH 7.4 and physiological temperature by the concomitant swelling and/or dissolution of the polymer.

The pH sensitive component comprises between about 1 to 30% by weight and preferably between about 2 to 20% by weight of the terpolymer.

As previously stated, there are problems formulating copolymers containing only temperature and pH sensitive properties. It is known that the LCST of polymers is affected by comonomers in such a way that the hydrophilic pH sensitive comonomer causes LCST to occur at higher temperatures. When the LCST rises to be above physiologic body temperature, the drug release is uncontrollable due to the increased solubility of the hydrogel matrix. However, hydrophobic comonomers lower the LCST.

It has been found that the problems associated with too high a LCST can be solved by incorporating into the polymer combination of pH and temperature sensitive monomers, a third monomer component which is not pH or temperature sensitive. Suitable monomer components for this purpose include any water insoluble monomers which are copolymerizable with the temperature sensitive and pH sensitive monomer components. Suitable monomers have the formula:

and styrene.

The hydrophobic component comprises between about 0.5 to 30% by weight and preferably between about 1 to 20% by weight of the terpolymer.

By adjusting the ratio of pH and hydrophobic components the LCST of the terpolymer can be controlled resulting in the desired properties for the terpolymer to be loaded with drugs. Furthermore, the hydrophobic component can also be adjusted to compensate for drug effects on the polymers, which depend on the amount, solubility and molecular weight of the drug loaded into the terpolymer matrix. The ratio of pH and temperature components and hydrophobic component are all important factors in determining the release rate of a solute or drug at pH 7.4 and body temperature. The ratio of components is also a factor in the shaping of a drug/polymer solution into the spherical dosage forms by dropping the solution into a bath maintained at a lower pH than the $pK_a$ of the pH sensitive component and above the LCST temperature of the terpolymer.

Therefore the terpolymer is preferably one made up by the copolymerization of the following monomer components having the following combined formula wherein the letter a, b and c represent numerals, or numeral ranges of monomer components in terms of percent by weight and not mole percent and the functional groups or integers represented by the other letters have the meanings given above:

Temperature Sensitive      pH Sensitive      Hydrophobic wherein $B^1$ and $B^2$ are members selected from the group consisting of hydrogen, halo, aryl, alkenyl and alkyl. $D^1$ is a member selected from the group consisting of hydrogen, lower alkyl, lower alkenyl and halo and $D^2$ is a member selected from the group consisting of a lower alkyl carboxylate, aryl, cyano and N-carbazole. $D^2$ can also be any other similar functional grouping which imparts the desired physical hydrophobic characteristics and is copolymerizable with the other components. Preferably $B^1$ and $B^2$ will be hydrogen, $D^1$ is either hydrogen or lower alkyl, methyl in particular, and $D^2$ is a member selected from the group consisting of a lower alkyl carboxylate, phenyl and cyano.

Exemplary of such monomers are lower alkyl acrylates or methacrylates, 1,3-diene monomers, α-methyl styrene, halogenated olefins, vinyl esters, acrylonitrile, methacrylonitrile, N-vinyl carbazole and the like. Preferred are alkyl acrylates and methacrylates having the following formula:

wherein R" is hydrogen or methyl and $R^3$ is a lower alkyl group having from 1 to 8 carbon atoms. Also preferred are styrene, α-methyl styrene, acrylonitrile and methacrylonitrile. Particularly preferred are the lower alkyl esters of acrylic acid and methacrylic acid such as methyl, ethyl, propyl, isopropyl, butyl and amyl acrylate and methacrylate In the terpolymer given above a is an numeral of between about 35 to 99 and preferably between about 80 to 98 which represents the weight percent of the temperature sensitive component, b is a numeral of between about 1 to 30 and preferably between about 2 to 20 which represents the weight percent of the pH sensitive component and c is a numeral of between about 0.5 to 30 and preferably between about 1 to 20 which represents the weight percent of the hydrophobic component.

In the above formula no attempt has been made to delineate the bonding between the various monomer components or to identify the order in which the various components occur in the terpolymer structure. It will be obvious to those skilled in the art that, in polymer formation, the positioning of the monomers will generally be random and any attempt to identify a polymer structure with specificity would not be feasible.

The terpolymers are synthesized by mixing the temperature and pH sensitive components and the hydrophobic component along with about 0.5 to 2% by weight of a radical or redox initiator, such as 2,2'-azobisisobutyronitrile [AIBN] or tert-butyl peroxyoctanoate [BPO] with a solvent, such as 1,4-dioxane or benzene, which is miscible with all of the components. Each component is carefully weighed and combined in a polymerization reactor where the contents are deoxygenated with dried nitrogen. The reactor is maintained at the desired polymerization temperature depending upon the decomposition temperature of the initiator, typically 50° to 100° C. for radical initiators and 4° to 30° C. for radox initiators. The polymerization is allowed to proceed for the desired period, e.g. from about 1 to 24 hours, after which the terpolymer solution is precipitated in a poor solvent, such as ether or n-hexane, which is miscible with the polymerization solvent and filtered. The resulting terpolymer can be dissolved in the same solvent as initially used and again precipitated in the poor solvent and filtered. This process can be repeated as many times as necessary to obtain a terpolymer of the desired purity and can then be air dried and finally vacuum dried. Each drying procedure will preferably take from about 8 to 23 hours.

The terpolymer may be loaded with a bioactive agent or drug in the following manner. From between about 0.1 to 200 milligrams of bioactive agent is dissolved per milliliter of solvent, such as phosphate buffered saline solution or water to form a solution. To this solution is then added from about 100 to 400 milligrams of terpolymer per milliliter of solution at room temperature. The aqueous mixture is cooled to about 4° C. and mildly agitated, such as by stirring or rotating in a flask, until the terpolymer is dissolved. Good results have also been obtained using distilled water. Appropriate bioactive agents are any low molecular weight drugs, proteins, polypeptides or other biologically active compounds. The invention is not drawn to any particular bioactive agent or class of agents provided they are functional with and can be loaded onto the terpolymer. If desired, additives, such as gastrointestinal absorption enhancers, enzyme inhibitors, protein stabilizing agents, plasticizers and the like, can also be incorporated onto the terpolymer. These additives can be loaded in a manner similar to the bioactive agents and can be added separately or in conjunction with the bioactive agent. The dissolved terpolymer/ bioactive agent solution is degassed by aspiration/nitrogen purging one or more times, as needed, and polymer beads loaded with bioactive agent are produced by drop precipitation as described below.

The amount of bioactive agents or additives which can be loaded on the terpolymers will depend on the degree of compatibility between the bioactive agent or additive and the terpolymer. These may be readily determined empirically. The bioactive agent, or bioactive agent plus additive, will generally make up between about 0.1 to 50 percent by weight of the loaded terpolymer with the terpolymer concentration varying between about 50 to 99.9 percent by weight. The amounts are limited only by compatibility and effectiveness. Assuming there is sufficient compatibility between the bioactive agent and the terpolymer there must obviously be sufficient bioactive agent present to be effective and not too much to present problems of toxicity. In other words, what is required is that the terpolymer be able to hold an effective dosage range of the active ingredient. In most instances the bioactive agent, including additives, will be present in amounts varying between about 0.5 to 40 weight percent and the terpolymer will be present in amounts ranging between about 60 to 99.5 percent by weight of the total drug/terpolymer composition.

Figure 1A:
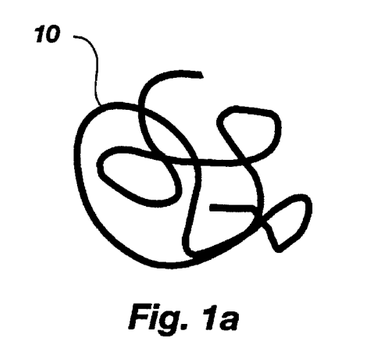
FIGS. 1a, 1b and 1c are representations of a terpolymer in a solution under different temperatures and pH conditions.
Figure 1B:
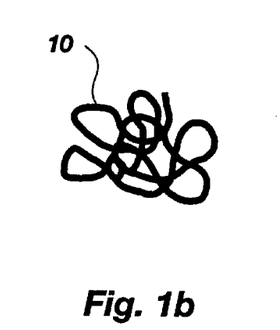
Figure 1C:
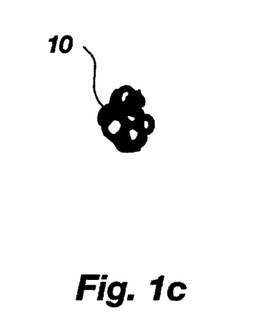
Figure 2A:
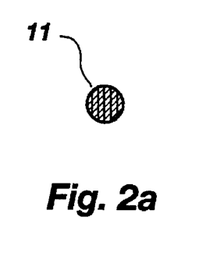
FIGS. 2a, 2b and 2c are representations of a drug-laden terpolymer precipitate prepared by drop precipitation showing the relative size of such precipitate in dry form or suspended in liquid at gastric and intestinal pH.
Figure 2B:
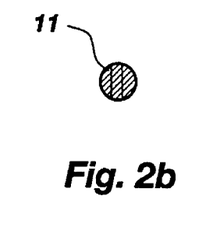
Figure 2C:
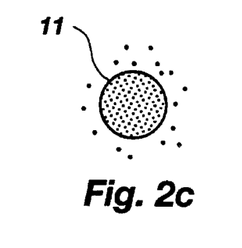

In order to explain the configuration of the terpolymer at various stages of drug loading and how it functions in use, reference is first made to FIGS. 1a–c and 2a–c. FIG. 1a shows an expanded terpolymer configuration 10 in solution at a pH of 7.4 and at a temperature below the LCST i.e. about 4° C. In this configuration the terpolymer is soluble and can freely intermix with bioactive compounds and other additives in aqueous solution. Another way to describe the terpolymer shown in FIG. 1a is that it has maximum solubility. When the temperature is raised above the LCST and the pH is maintained at about 7.4 there is a partial tightening of the terpolymer chain as represented by polymer configuration 10 in FIG. 1b. In this state the terpolymer is not soluble. Nevertheless, the terpolymer will still swell in aqueous solutions. However, upon lowering the pH to between about 2–3, the pH sensitivity functions to make the terpolymer more hydrophobic and therefore it precipitates in aqueous solutions, particularly at physiologic temperatures. This is represented by the polymer configuration 10 shown in FIG. 1c. A somewhat analogous situation is shown in FIGS. 2a–c. FIG. 2a shows the configuration of a precipitated drug-laden terpolymer 11 after air or vacuum drying. FIG. 2b shown the same drug-laden terpolymer 11 in a gastric fluid atmosphere, i.e. at a temperature of about 37° C. and a pH of about 2–3. Therefore, the configuration of the drug-laden terpolymer 11 in FIG. 2b is similar to the polymer configuration 10 illustrated in FIG. 1c in that both are at the same temperature and pH. In this configuration the terpolymer is not soluble and will not release any significant amount of drug loaded within its matrix. However, upon reaching the small intestine where the pH is raised the drug-laden terpolymer 11 will swell as shown in FIG. 2c allowing release of the drug for intestinal absorption. The drug-laden polymer 11 represented by FIG. 2c is analogous to the polymer configuration 10 represented in FIG. 1b in that both are at the same temperature and pH. FIGS. 1a–c represent the stages of a terpolymer during drug loading and FIGS. 2a–c represent the stages of a drug/terpolymer from oral ingestion to drug release.

Figure 3:
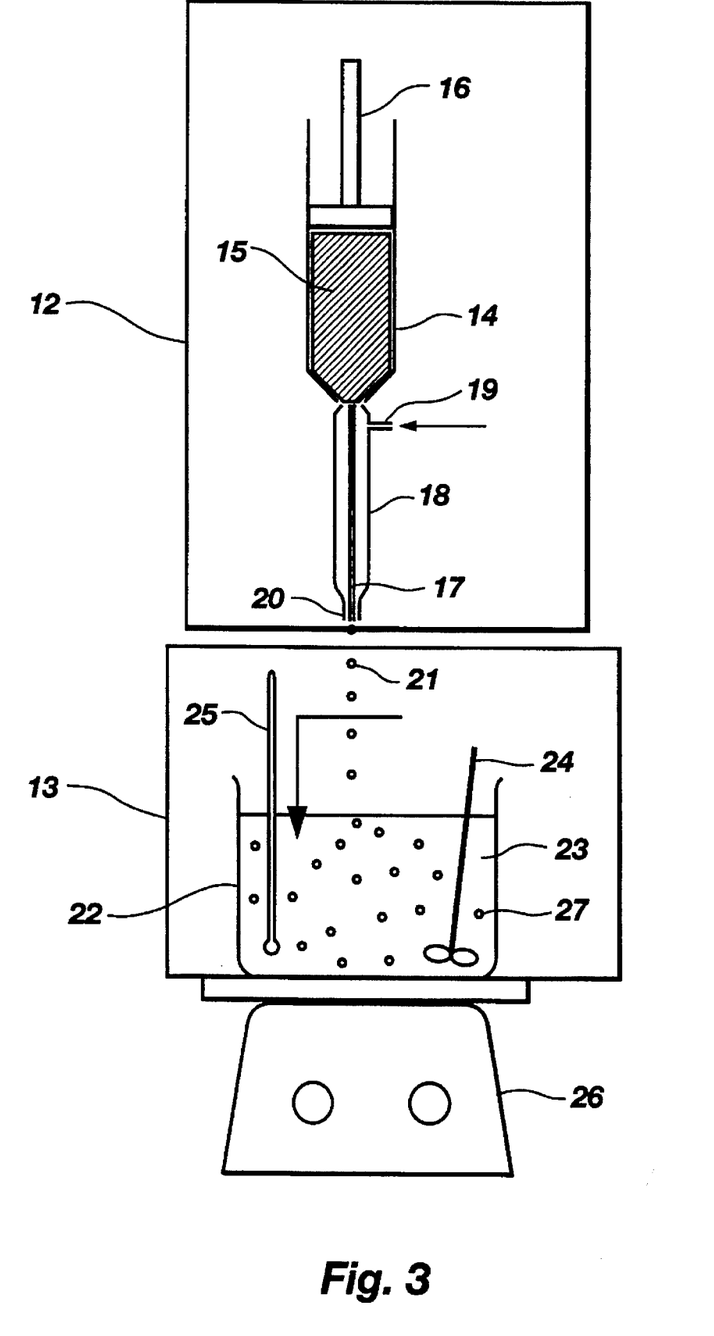
FIG. 3 is a graphic representation of one means for preparing drug-laden terpolymer precipitates by drop precipitation from cold polymer/drug solutions into a buffered low pH water bath maintained above the LCST of the terpolymer.

The method of preparation of a drug-laden terpolymer is represented in FIG. 3. Box 12 schematically represents a soluble drug terpolymer solution and means for dispensing this solution as drops. Box 13 schematically represents the precipitation of the drug/terpolymer drops in a low pH buffered water bath. Into the hollow interior (reservoir) of a cylinder 14 is placed a drug/terpolymer solution 15 prepared as described above. The solution is maintained at a temperature below the LCST and at a pH above about 7.0. A piston 16 slides inside the cylinder and controls the discharge of drug/terpolymer solution through a needle 17 at the opposite end of the cylinder. The end portion of needle 17 extends into an air chamber 18. Air chamber 18 contains an upper inlet 19 and an outlet 20 adjacent the end of needle 17. The solution is dispensed at a constant rate from the end of the needle 17. Air flowing through chamber 18 from inlet 19 through outlet 20 forces small droplets 21 of drug/ terpolymer solution off the end of the needle when the droplets reach a predetermined critical diameter. Variables which influence droplet size, and subsequently bead size, include the viscosity and surface tension of the polymer solution, needle diameter and air flow rate through chamber 18. Since the needle diameter is a constant and the viscosity and surface tension of a given polymer solution are fixed, only the air flow rate through chamber 18 is a variable which can be controlled to provide droplets, and subsequently beads 27, of a predetermined size when droplets 21 fall into a container 22 holding a buffered water bath 23. The bath is stirred continuously with a stirrer 24 and is maintained at a relatively constant temperature, as registered by thermometer 25, by a heater 26. The pH of the bath is maintained at a pH below about 4 and preferably about 2–3 and at a temperature which is above the LCST of the drug/terpolymer solution. When the droplets 21 fall into the low pH solution at a temperature above the LCST, the drug/terpolymer droplets precipitate into solid particles 27. The formed particles or beads 27 can be porous or dense spheres or shell capsules depending on variable factors including pH and temperature of the bath and polymer and drug concentration. The drug/terpolymer particles are removed from the water bath by filtration and dried by air, vacuum or freeze drying techniques.

Figure 4:
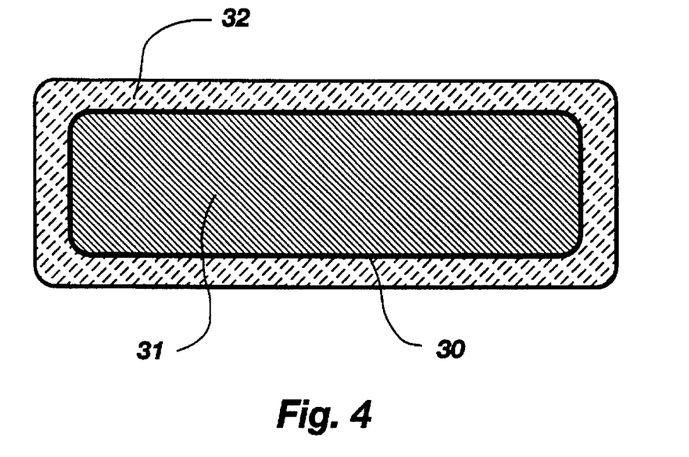
FIG. 4 is a cross sectional view of a gelatin capsule containing a drug which has been coated with a terpolymer.

Another embodiment is illustrated in FIG. 4 which shows a capsule (or matrix) 30 holding a drug 31. The capsule is coated with a terpolymer coating 32 which will prevent dissolution of the capsule in the acidic environment of the stomach. The terpolymers, as described above, are freely soluble in alcohol/plasticizer mixtures. Such alcoholic solutions can be used for the coating of capsules, tablets or other matrices containing drugs. The small amount of plasticizer will prevent cracks in the glassy terpolymer after coating and drying. The coating can be applied in a conventional manner such as by spraying, dipping or brushing the matrix.

Figure 5A:
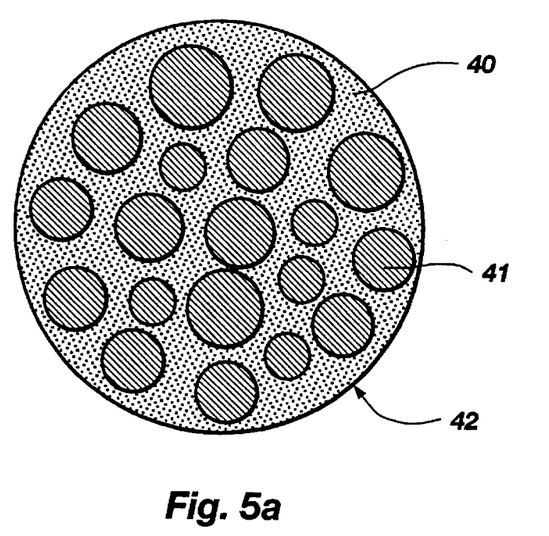
FIG. 5a and 5b are cross sectional views of a terpolymer bead showing drug containing particles embedded in or coated by a terpolymer matrix.
Figure 5B:
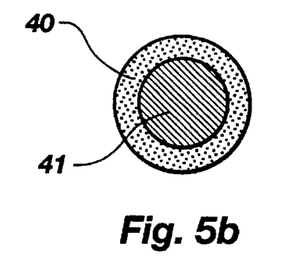

FIGS. 5a and 5b shows yet another embodiment consisting of terpolymer coated microparticles or colloidal particles. In this embodiment the terpolymers 40 are put in solution at temperatures below the LCST of the terpolymer in the manner as described for the drug/terpolymers in FIG. 3 and drug microparticles 41 are suspended therein. Upon dropping a solution of terpolymer containing the suspended drug microparticles into a water bath which raises the temperature above the LCST and lowers the pH the resulting bead precipitate 42 shown in FIG. 5a consisting of microparticles 41 embedded in a terpolymer matrix 40 is formed, or, as shown in FIG. 5b, a single drug particle 41 coated by the terpolymer 40. In either event, the terpolymer serves as a diffusional barrier.

From the above it is apparent that the bioactive agent can be constructed or made up in various unit dosage forms such as capsules, tablets and particulates. By "envelop" is meant that the unit dosage form is either surrounded by a coating of the terpolymer or embedded within a terpolymer matrix.

There follows a series of examples which serve to portray the invention. However, these examples are illustrative only and are not to be construed as limiting the invention in scope.

EXAMPLE 1

Terpolymer Synthesis

In this example four terpolymers were prepared. The temperature sensitive monomer component utilized was N-isopropylacrylamide (NIPAAm), the pH sensitive component was acrylic acid (AAc) and the hydrophobic component was butylmethacrylate (BMA). The initiator, 2,2'-bisisobutyronitrile (AIBN) was used. In preparing the terpolymers, the monomers in weights given the Table 1 and 0.414 mg. of initiator were carefully weighed and placed into a three neck flask having a nitrogen inlet, thermometer and reflux condenser and holding 300 mls of dioxane. The contents in the flask were degassed under nitrogen and the flask slowly heated to a reaction temperature of 60° C. The polymerization was allowed to proceed overnight after which the polymer solution was precipitated in n-hexane, filtered and air dried. Table 1 shows the composition of terpolymers A–D both in terms of monomer weights used and percent by weight of each monomer component.

TABLE 1

| Terpolymer | NIPAAm grams | (% w) | AAc grams | (% w) | BMA grams | (% w) |
|---|---|---|---|---|---|---|
| A | 18.00 | (86.73) | 1.332 | (6.43) | 1.422 | (6.85) |
| B | 18.00 | (91.02) | 1.243 | (6.29) | 0.532 | (2.69) |
| C | 18.00 | (90.08) | 1.580 | (7.91) | 0.403 | (2.01) |
| D | 18.00 | (88.17) | 2.280 | (11.17) | 0.136 | (0.66) |

Since these polymers are soluble in aqueous solutions at temperatures below their LCST they can be dissolved and reprecipitated for purposes of both purification and drug loading or mixing.

EXAMPLE 2

Terpolymer/Dextran Solution

Solutions were made using polymers A, B, C and D from Example 1. First, a solution was made by dissolving 300 mg polymer per ml of phosphate buffered saline (PBS) at pH 8 and 4° C. This solution was rotated in a flask for several days to completely dissolve the polymer. Into a small vial was weighed out 0.5 grams of the polymer solution and dextran (mw 3860) was added at a concentration of between 25 to 30 mg per ml of polymer solution. The polymer/dextran mixture was then agitated by shaking for about two hours to bring about a uniform drug/terpolymer solution.

EXAMPLE 3

Terpolymer/Insulin Solution

The procedure of Example 2 was repeated using polymer B from Example 1 as the terpolymer and insulin as the drug. Insulin (0.3% wt of polymer solvated) was added to the polymer solution and agitated until a uniform solution was obtained.

EXAMPLE 4

Terpolymer/Drug Beads

By following the procedure illustrated in FIG. 3, the terpolymer/drug solutions of Example 2 and 3 were dropped into a buffered water bath at a pH of about 2–3 and at a temperature above the LCST of the terpolymer. The formed terpolymer/drug beads were freeze dried resulting in a bead diameter of about 1 mm. Based on the amount of drugs added to the terpolymer solution, dextran loss caused by leaching during the bead formation ranged between about 10 to 25% and insulin loss was less than 10%.

EXAMPLE 5

Cumulative Dextran Release

The in vitro release of dextran (mw 3860) from the terpolymer/dextran beads formed as shown in Examples 2 and 4 was determined in water at a pH of 2 and also at a pH 7.4 at a temperature of 37° C. The data in the following table shows the cumulative mg of dextran released per mg of terpolymer/dextran beads over a period of 24 hours at pH 7.4.

TABLE 2

| Terpolymer | Cumulative Dextran Release (mg/mg beads) Time (hrs) | | | | | |
|---|---|---|---|---|---|---|
| | 0.5 | 1.0 | 2.0 | 4.0 | 8.0 | 24 |
| A | 0.052 | 0.055 | 0.055 | — | — | — |
| B | 0.019 | 0.024 | 0.042 | 0.058 | 0.073 | 0.073 |
| C | 0.005 | 0.007 | 0.010 | 0.016 | 0.022 | 0.042 |
| D | 0.002 | 0.003 | 0.004 | 0.006 | 0.006 | 0.013 |

The release of dextran at pH 2 was negligible, i.e. less than 0.002 mg dextran/mg beads over a 24 hour period. This example demonstrates the ability of terpolymer A, B, C and D to prevent the release of dextran at low pH, such as encountered in gastric fluid, but which is sensitive to the release of dextran at the higher pH encountered in the intestinal tract.

EXAMPLE 6

Cumulative Insulin Release

The in vitro release of insulin from the terpolymer B/insulin beads formed as shown in Examples 3 and 4 was determined in water at a pH 7.4 at a temperature of 37° C. The data in the following table shows the cumulative mg of insulin released per mg of terpolymer B/insulin beads over a period of 24 hours at pH 7.4.

TABLE 3

| Time (hrs) | Cumulative Insulin Release (mg/mg beads) | | | | | | |
|---|---|---|---|---|---|---|---|
| | 0.5 | 1.0 | 2.0 | 4.0 | 8.0 | 16.0 | 24.0 |
| Terpolymer B | 0.0009 | 0.0015 | 0.0020 | 0.0027 | 0.0028 | 0.0031 | 0.0036 |

The release of insulin at pH 2 was negligible over the 24 hour period. This example demonstrates the ability of the terpolymer to prevent the release of insulin at low pH, such as encountered in gastric fluid, but which is sensitive to the release of insulin at the higher pH encountered in the intestinal tract.

The above specification describes the invention in terms to enable one skilled in the art to practice it but is not an exhaustive statement of specific drugs which can be utilized and loaded onto the terpolymers. Neither are all terpolymers which may be prepared specifically shown. Moreover, it will be apparent to one skilled in that art that various modifications can be made without departing from the scope of the invention. Therefore, the invention is limited in scope only by the following claims and their functional equivalents.

I claim:

1. An oral bioactive agent containing polymer composition sensitive to pH and temperature for passing a bioactive agent though the stomach of a warm blooded animal in a protected form and releasing said bioactive agent to the intestinal tract of said animal comprising:

(a) between about 0.1 to 50 percent by weight of a bioactive agent loaded onto;

(b) between about 50 to 99.9 percent by weight of a pH and temperature sensitive terpolymer having the formula:

where a is a numeral of between about 35 to 99, b is a numeral of between about 1 to 30 and c is a numeral of between about 0.5 and 30 wherein a, b and c total 100 and are representative of percent by weight of each monomer component in the terpolymer; R is a member selected from the group consisting of hydrogen and methyl; $R^1$ is a member selected from the group consisting of lower alkyl and lower alkoxyalkyl; $R^2$ is a member selected from the group consisting of hydrogen, lower alkyl and lower alkoxyalkyl with the proviso that $R^1$ and $R^2$ can combine as an alkylene —$(CH_2)_n$— chain to form a N-cyclic structure; n is an integer of 4 to 6; R' is a member selected from the group consisting of hydrogen, lower alkyl, lower alkenyl, aryl, substituted aryl, lower alkoxy, aryloxy, hydroxy, carboxyalkyl, amino, substituted amino, amido and substituted amido; A is a member selected from the group consisting of lower alkylene, lower alkenylene, phenylene and substituted derivatives thereof; p is an integer of 0 to 3; $Y^1$ is a member selected from the group consisting of hydrogen, lower alkyl, lower alkenyl, aryl, carboxyalkyl, hydroxyalkyl, hydroxy and chloro; $Y^2$ is a member selected from the group consisting of hydrogen, lower alkyl, lower alkenyl, carboxy, carboxyalkyl, carboxyalkenyl, carboxyalkenylaryl, hydroxy, hydroxyalkyl, aroyl, carbamoyl, N- and N,N- alkyl, alkenyl or aryl substituted carbamoyl, alkyl carbamoyl, 5-norborneyl and chloro; $B^1$ and $B^2$ are each members selected from the group consisting of hydrogen, halo, aryl, alkenyl and alkyl; $D^1$ is a member selected from the group consisting of hydrogen, lower alkyl, lower alkenyl and halo and $D^2$ is a member selected from the group consisting of a lower alkyl carboxylate, aryl, cyano and N-carbazole, with the proviso that the term lower references a carbon grouping containing not more than 8 carbon atoms; and wherein said bioactive agent is combined with said terpolymer in solution at a temperature below the lower critical solution temperature of said terpolymer followed by the raising of the temperature of said combined terpolymer/bioactive agent solution to above the lower critical solution temperature of said terpolymer by means of introducing said terpolymer/bioactive agent solution into a bath solution causing said terpolymer/bioactive agent solution to precipitate into particles which are then separated from said bath solution and dried.

2. An oral bioactive agent containing polymer composition according to claim 1 wherein the bioactive agent comprises between about 0.5 to 40 percent by weight and the terpolymer comprises between about 60 and 99.5 percent by weight of the polymer composition.

3. An oral bioactive agent containing polymer composition according to claim 2 wherein a is an numeral of between about 80 and 98, b is a numeral of between about 2 and 20 and c is a numeral of between about 1 and 20.

4. An oral bioactive agent containing polymer composition according to claim 3 wherein p is 0 and R' is a member selected from the group consisting of hydrogen and lower alkyl.

5. An oral bioactive agent containing polymer composition according to claim 4 wherein $Y^1$ is a member selected from the group consisting of hydrogen, lower alkyl, lower alkenyl, hydroxy and lower carboxyalkyl and $Y^2$ is a member selected from the group consisting of hydrogen, lower alkyl, lower alkenyl, carboxy, carbamoyl and substituted carbamoyl.

6. An oral bioactive agent containing polymer composition according to claims 5 wherein $B^1$ and $B^2$ are hydrogen, $D^1$ is a member selected from the group consisting of hydrogen and lower alkyl and $D^2$ is a member selected from the group consisting of a lower alkyl carboxylate, phenyl and cyano.

7. An oral bioactive agent containing polymer composition according to claim 3 wherein the monomer component represented by the formula:

is a temperature sensitive monomer component selected from the group consisting of N-isopropylacrylamide, N,N-diethylacrylamide, acryloylpiperidine, N-ethylmethacrylamide, N-n-propylacrylamide, N-(3'-methoxypropyl)acrylamide and mixtures thereof.

8. An oral bioactive agent containing polymer composition according to claim 7 wherein the monomer component represented by the formula:

is a pH sensitive monomer component selected from the group consisting of 2-acetamidoacrylic acid, acrylic acid, cis-aconitic acid, trans-aconitic acid, allylacetic acid, 2-allylphenoxyacetic acid, β-benzoacrylic acid, 2-chloroacrylic acid, crotonic acid, N,N-di-n-butylmaleamic acid, fumaric acid, N,N-diethylmaleamic acid, dihydroxymaleic acid, itaconic acid, 3,3-dimethylacrylic acid, N-ethylmaleamic acid, trans-2-hexenoic acid, trans-3-hexenoic acid, methacrylic acid, maleic acid, 5-norbornene-2-acrylic acid, trans-2-pentenoic acid, 1,4-phenylenediacrylic acid, N-phenylmaleamic acid, vinylacetic acid, 2,4-hexadienonic acid, 4-vinylbenzoic acid, 2-vinylpropionic acid and mixtures thereof.

9. An oral bioactive agent containing polymer composition according to claim 8 wherein the monomer component represented by the formula:

is a hydrophobic monomer component selected from the group consisting of alkyl acrylates and methacrylates having the formula $CH_2=CR''-COOR^3$ wherein R'' is hydrogen or methyl and $R^3$ is a lower alkyl having from 1 to 8 carbon atoms, styrene, α-methyl styrene, acrylonitrile, methacrylonitrile and mixtures thereof.

10. An oral bioactive agent containing polymer composition according to claim 9 wherein the temperature sensitive monomer component is a member selected from the group consisting of N-isopropylacrylamide, N,N-diethylacrylamide and N-n-propylacrylamide.

11. An oral bioactive agent containing polymer composition according to claim 10 wherein the pH sensitive monomer component is a member selected from the group consisting of acrylic and methacrylic acid.

12. An oral bioactive agent containing polymer composition according to claim 11 wherein the hydrophobic monomer component is a member selected from the group consisting of methyl acrylate, ethyl acrylate, propyl acrylate, isopropyl acrylate, butyl acrylate, amyl acrylate, methyl methacrylate, ethyl methacrylate, propyl methacrylate, isopropyl methacrylate, butyl methacrylate, amyl methacrylate and styrene.

13. An oral bioactive agent containing polymer composition according to claim 12 wherein the temperature sensitive monomer component is N-isopropylacrylamide, the pH sensitive monomer component is acrylic acid and the hydrophobic monomer component is butyl methacrylate.

14. An oral composition sensitive to pH and temperature for passing a bioactive agent though the stomach of a warm blooded animal in a protected form and releasing said bioactive agent to the intestinal tract of said animal comprising:

(a) a unit dosage form of a bioactive agent enveloped by;

(b) a pH and temperature sensitive terpolymer having the formula:

where a is a numeral of between about 35 to 99, b is a numeral of between about 1 to 30 and c is a numeral of between about 0.5 and 30 wherein a, b and c total 100 and are representative of percent by weight of each monomer component in the terpolymer; R is a member selected from the group consisting of hydrogen and methyl; carbamoyl, 5-norborneyl and chloro; $B^1$ and $B^2$ are each members selected from the group consisting of hydrogen, halo, aryl, alkenyl and alkyl; $D^1$ is a member selected from the group consisting of hydrogen, lower alkyl, lower alkenyl and halo and $D^2$ is a member selected from the group consisting of a lower alkyl carboxylate, aryl, cyano and N-carbazole with the proviso that the term lower references a carbon grouping containing not more than 8 carbon atoms.

15. An oral composition according to claim 14 wherein said unit dosage form is a capsule which is surrounded by a coating of said terpolymer.

16. An oral composition according to claim 14 wherein said unit dosage form is a tablet which is enveloped by a coating of said terpolymer.

17. An oral composition according to claim 14 wherein said unit dosage form consists of particulates which are embedded in a matrix of said terpolymer.

* * * * *